US012305325B2

(12) United States Patent
Bates et al.

(10) Patent No.: US 12,305,325 B2
(45) Date of Patent: *May 20, 2025

(54) ODOR CONTROL COMPOSITION CONCENTRATES

(71) Applicant: MICROBAN PRODUCTS COMPANY, Huntersville, NC (US)

(72) Inventors: Daniel Bates, Charlotte, NC (US); Ryan Scott, Charlotte, NC (US); Ishmell Williams, Charlotte, NC (US); Lillian Stephens, Charlotte, NC (US)

(73) Assignee: MICROBAN PRODUCTS COMPANY, Huntersville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/737,162

(22) Filed: Jun. 7, 2024

(65) Prior Publication Data

US 2024/0410107 A1 Dec. 12, 2024

Related U.S. Application Data

(60) Provisional application No. 63/471,576, filed on Jun. 7, 2023.

(30) Foreign Application Priority Data

Jun. 26, 2023 (NL) .................................... 2035180

(51) Int. Cl.
| | | |
|---|---|---|
| *D06M 13/00* | (2006.01) | |
| *A61L 9/013* | (2006.01) | |
| *A61L 9/014* | (2006.01) | |
| *D06M 11/77* | (2006.01) | |
| *D06M 13/224* | (2006.01) | |

(52) U.S. Cl.
CPC ........... *D06M 13/005* (2013.01); *A61L 9/013* (2013.01); *A61L 9/014* (2013.01); *D06M 11/77* (2013.01); *D06M 13/2243* (2013.01); *A61L 2209/22* (2013.01)

(58) Field of Classification Search
CPC ................................................ D06M 13/2243
See application file for complete search history.

(56) References Cited

U.S. PATENT DOCUMENTS

| 9,605,230 B2 * | 3/2017 | Bouvier ............... C10M 125/26 |
| 2008/0128941 A1 * | 6/2008 | Lopez ...................... D01D 5/30 |
| | | 264/172.11 |
| 2021/0009923 A1 * | 1/2021 | Miller ...................... C11D 3/20 |

FOREIGN PATENT DOCUMENTS

| WO | 02090481 A1 | 11/2002 | |
| WO | 2015167221 A1 | 11/2015 | |
| WO | WO2020065541 A1 * | 4/2022 | ............... A61K 8/06 |

OTHER PUBLICATIONS

Hamza Aysan et al., Use of chabazite, a naturally abundant zeolite, for the investigation of the adsorption kinetics and mechanism of methylene blue dye, Microporous and Mesoporous Materials, vol. 235, 2016, pp. 78-86, ISSN 1387-1811 (Year: 2016).*
Baltimore Innovations, 3A Supersiv® Paste, Zeolite Molecular Sieve Paste, publication date: May 17, 2022 (Year: 2022).*
Baltimore Innovations (Product Data Sheet evidencing prior art date), 3A Supersiv® Paste, Zeolite Molecular Sieve Paste, publication date: May 17, 2022 (Year: 2022).*
Proceco Integrated Cleaning Systems, Aqueous Cleaning Fundamentals, publication date: May 21, 2021 (Year: 2021).*
International Search Report and Written Opinion issued Oct. 25, 2024 for PCT/US2024/032978 (14 Pages).

* cited by examiner

*Primary Examiner* — Mark V Stevens
*Assistant Examiner* — Alparslan Asan
(74) *Attorney, Agent, or Firm* — Shumaker, Loop & Kendrick, LLP

(57) ABSTRACT

An odor control concentrate composition including a plant derived non-volatile triglyceride that binds and/or neutralizes organic malodor molecules; and a zeolite that binds and/or neutralize organic malodor molecules. The odor control concentrate composition may be diluted and further applied to a textile/textile material. Textiles having the odor control compositions applied thereon and/or treated with the odor control compositions in which the treated textile binds, neutralizes, and/or reduces odor(s) associated with odor molecules for a prolonged period of time (e.g., up to twenty-five (25) wash cycles, for several months, for several years, or any combination thereof).

5 Claims, No Drawings

ODOR CONTROL COMPOSITION CONCENTRATES

TECHNICAL FIELD

The present invention relates generally to the field of odor control compositions and textiles treated with the same. More particularly, odor control compositions including plant derived non-volatile triglycerides that binds and/or neutralizes organic malodor molecules; and a high surface area essential mineral (HSAEM) that binds and/or neutralize organic malodor molecules for prolonged periods of time. In certain aspects, the odor control compositions are not intended for consumer use and/or for application to a textile by a consumer. Instead, textiles are treated with the odor control compositions during manufacture to form a treated textile in which the treated textile binds and/or neutralizes the organic malodor molecules for a prolonged period of time (e.g., up to twenty-five (25) wash cycles, for several months, for several years, or any combination thereof).

BACKGROUND

The current field of textile odor reduction on textile materials (e.g., dry textile materials and articles) has a limited number of options and formulations, which mostly utilize heavy metals or nanomaterials to reduce specific odors. These heavy metal based formulations and nanomaterials have many drawbacks, which include being environmentally harsh. In particular, these materials are typically used in conjunction with a polymer/polymer blend to adhere to textiles, but overtime these metals wash out of the textiles and leach into the soil and ground water, which, in high concentrations, are harmful to plants and animals. Moreover, WO 2015/167221 and WO 2002/090481 disclose various perfume, laundry, and deodorant formulations that are applied by a consumer to textiles to impart temporary/transient odor control and/or odor masking properties. However, these formulations do not withstand repeated washings/cleanings and further do not impart odor control and/or odor masking for prolonged periods of time.

SUMMARY

Accordingly, there is a need to provide environmentally friendly odor control compositions/formulations that avoid the use of heavy metals and nanomaterials. In certain aspects, disclosed herein are environmentally friendly odor control compositions/formulations that are just as effective, if not more effective, than the currently known heavy metal and nanomaterial formulations. The compositions, articles, and methods disclosed herein overcome the above-mentioned problems observed with heavy metal and nanomaterial compositions by providing environmentally friendly compositions that utilize a combination of plant derived non-volatile triglycerides and zeolites that synergistically interact with one another to reduce (by binding and neutralizing and/or reducing odors associated with) certain organic malodors (i.e., odors often associated with human body odor including odorous human secretions and/or by-product produced by bacteria and/or yeast found on the human body) on textile materials for a prolonged period of time. The organic malodors include, for example, isovaleric acid, ammonia, acetic acid, and nonenal.

Moreover, and unlike the above-mentioned heavy metals and nanomaterial compositions, the compositions disclosed herein remain within a textile longer than formulations that include heavy metals and nanomaterials because the disclosed compositions are wash resistant. This wash resistance advantageously allows for the disclosed compositions to remain in a textile for prolonged periods of time (e.g., 25 wash cycles, several months, or up to a year) and impart odor control in and on the textile reducing odors associated with isovaleric acid, ammonia, acetic acid, and nonenal. Without wishing to be bound by theory, it is thought that the insolubility of the plant derived non-volatile triglycerides and high surface area of the zeolites prevent the disclosed compositions from washing out of the textile material/textile fabric thereby allowing for repeated uses and prolonged odor control for textile materials having the disclosed compositions applied thereon.

In certain aspects, disclosed is an odor control concentrate composition comprising: (a) an plant derived non-volatile triglycerides (at an effective amount) that binds and/or neutralizes organic malodor molecules; and (b) a zeolite (at an effective amount) that binds and/or neutralize organic malodor molecules. The plant derived non-volatile triglycerides disclosed herein advantageously function to bind and/or neutralize the organic molecules while concurrently functioning to adhere the zeolite to the textile material. In certain aspects, the composition may further include water therein, and when included, water is present at a concentration ranging from 10 wt % to 40 wt % of the composition in which any endpoint falling therein may serve as an endpoint for additional ranges, additional ranges may include, for example, from 10 wt % to 30 wt %, from 15 wt % to 27.5 wt %, from 15 wt % to 25 wt %, from 17.5 wt % to 25 wt %. In certain aspects, the compositions disclosed herein exclude dextrins, cyclodextrins, and/or highly branched cyclodextrins as well as effervescent systems (e.g., systems that form/generate gas from, for example, an acid source and a carbon dioxide source). In certain aspects, the present composition comprises less than 0.1 wt. % or even less than 0.01 wt. % of dextrins, such as cyclic dextrins, in particular high branched cyclic dextrins. In certain aspects, the present composition comprises less than 0.1 wt. % or even less than 0.01 wt. % of an effervescing composition, in particular comprising an acid source and a carbon dioxide source. Furthermore, the disclosed compositions are not laundry additives/laundry detergent additives intended for consumer use.

In certain aspects, the plant derived non-volatile triglycerides is present in the odor control concentrate composition (before application to the textile) at a concentration ranging from 18 wt % of the composition to 40 wt % of the composition in which any endpoint falling therein may serve as an endpoint for additional ranges, additional ranges may include, for example, from 20 wt % to 35 wt %, from 25 wt % to 40 wt %, from 25 wt % to 30 wt %, from 18 wt % to 30 wt %.

In certain aspects, the zeolite is present in the odor control concentrate composition (before application to the textile) at a concentration ranging from 10 wt % of the composition to 50 wt % of the composition in which any endpoint falling therein may serve as an endpoint for additional ranges, additional ranges may include, for example, from 15 wt % to 50 wt %, from 20 wt % to 45 wt %, from 25 wt % to 40 wt %, from 30 wt % to 40 wt %.

In certain aspects, the plant derived non-volatile triglycerides and zeolite are present at a ratio of wherein the plant derived non-volatile triglycerides and zeolite are present at a ratio of 3:1 to 1:3, 2:1 to 1:2 more preferably 1.5:1 to 1:1.5, most preferably 1:1.

In certain aspects, the plant derived non-volatile triglycerides comprises aloe oil (also referred to as "aloe vera oil" in the Specification), castor oil, hemp seed oil, flax seed oil, or any combination thereof. In certain aspects, the plant derived non-volatile triglycerides comprises at least two of aloe oil, castor oil, hemp seed oil, flax seed oil, and canola oil. In certain aspects, plant derived non-volatile triglycerides comprises at least three of aloe oil, castor oil, hemp seed oil, flax seed oil, and canola oil. In certain aspects, the plant derived non-volatile triglycerides comprises aloe oil, castor oil, hemp seed oil, flax seed oil, and canola oil. When there are two plant derived non-volatile triglycerides present in the concentrate compositions, the oils may be present in a 5:1 to 1:5 ratio, a 3:1 to 1:3 ratio, or a 1:1 ratio.

In certain aspects, the zeolite and more particularly zeolite is chabazite and/or pentasil. In certain aspects, the odor control concentrate composition also includes one or more surfactants, binders, thixotropic agents, dispersants, or any combination thereof to aid in dispersion of the components within, for example, the concentrated and/or diluted composition(s) and/or for application and/or binding of the composition to the textile material.

In certain aspects, the odor control concentrate composition is a liquid. In certain aspects, the concentrate composition is an emulsion.

In certain aspects, the odor control concentrate composition is a water in oil emulsion or an oil in water emulsion that is configured to be applied to a textile and/or to treat a textile and subsequently dried/cured thereon to impart prolonged odor control (e.g., a predetermined number of wash cycles including 10 wash cycles and/or 25 wash cycles and/or a predetermined period of time for several months to several years post-treatment and drying/curing on the textile).

In certain aspects, wherein the organic malodor/odor molecules comprise ammonia, acetic acid, isovaleric acid, nonenal, or any combination thereof.

In certain aspects, the organic malodor/odor molecules comprise at least two of ammonia, acetic acid, nonenal, and isovaleric acid.

In certain aspects, the organic malodor/odor molecules comprises ammonia, acetic acid, nonenal, and isovaleric acid.

Also disclosed herein are textile coatings/textile coating compositions comprising: (a) a plant derived non-volatile triglycerides (at an effective amount) that binds and/or neutralizes organic odor molecules (effective amount(s) to bind and/or neutralize organic odor molecules); and (zeolite (at an effective amount) that binds and/or neutralizes organic odor molecules (effective amount(s) to bind and/or neutralize organic odor molecules). The plant derived non-volatile triglycerides disclosed herein advantageously function to bind and/or neutralize the organic molecules while concurrently functioning to adhere the zeolite to the textile material. In certain aspects, the textile coatings/textile coating compositions disclosed herein exclude dextrins, cyclodextrins, and/or highly branched cyclodextrins, as well as effervescent systems (e.g., systems that form/generate gas from, for example, an acid source and a carbon dioxide source). Furthermore, the disclose compositions are not laundry additives/laundry detergent additives intended for consumer use.

In certain aspects, the plant derived non-volatile triglycerides is present in the odor control composition (before application to the textile) at a concentration ranging from 18 wt % of the composition to 40 wt % of the composition in which any endpoint falling therein may serve as an endpoint for additional ranges, additional ranges may include, for example, from 20 wt % to 35 wt %, from 25 wt % to 40 wt %, from 25 wt % to 30 wt %, from 18 wt % to 30 wt %.

In certain aspects, the zeolite is present in the odor control composition (before application to the textile) at a concentration ranging from 10 wt % of the composition to 50 wt % of the composition in which any endpoint falling therein may serve as an endpoint for additional ranges, additional ranges may include, for example, from 15 wt % to 50 wt %, from 20 wt % to 45 wt %, from 25 wt % to 40 wt %, from 30 wt % to 40 wt %.

In certain aspects, the plant derived non-volatile triglycerides and zeolite are present at a ratio of 3:1 to 1:3, 2:1 to 1:2 more preferably 1.5:1 to 1:1.5, most preferably 1:1.

In certain aspects, the plant derived non-volatile triglycerides comprise aloe oil, castor oil, hemp seed oil, flax seed oil, canola oil, or any combination thereof. In certain aspects, the plant derived non-volatile triglycerides comprises at least two of aloe oil, castor oil, hemp seed oil, flax seed oil, and canola oil. In certain aspects, plant derived non-volatile triglycerides comprises at least three of aloe oil, castor oil, hemp seed oil, flax seed oil, and canola oil. In certain aspects, the plant derived non-volatile triglycerides comprises aloe oil, castor oil, hemp seed oil, flax seed oil, and canola oil. When there are two plant derived non-volatile triglycerides present in the compositions, the oils may be present in a 5:1 to 1:5 ratio, a 3:1 to 1:3 ratio, or a 1:1 ratio.

In certain aspects, the zeolite is and more particularly zeolite chabazite and/or pentasil. In certain aspects, one or more surfactants, binders, thixotropic agents, dispersants, or any combination thereof may be included.

In certain aspects, the composition is a liquid. In certain aspects, the composition is an emulsion. In certain aspects, the composition is a water in oil emulsion or an oil in water emulsion, containing between 10-30% water in which any endpoint falling therein may serve as an endpoint for additional ranges, that is configured to be applied to a textile and/or to treat a textile and subsequently dried/cured thereon to impart prolonged odor control (e.g., a predetermined number of wash cycles including 10 wash cycles and/or 25 wash cycles and/or a predetermined period of time for several months to several years post-treatment and drying/curing on the textile).

In certain aspects, wherein the organic malodor molecules comprise ammonia, acetic acid, isovaleric acid, nonenal, or any combination thereof.

In certain aspects, the organic malodor molecules comprise at least two of ammonia, acetic acid, nonenal, and isovaleric acid.

In certain aspects, the organic malodor molecules comprises ammonia, acetic acid, nonenal, and isovaleric acid.

Also disclosed herein are textiles having at least one of the above-mentioned odor control compositions applied thereon (and/or treated therewith). In certain aspects, the textiles are subsequently dried and/or cured such that the above-mentioned odor control compositions are permanently adhered thereon and impart prolonged odor control. In certain aspects also disclosed are textiles having the odor control compositions applied thereon and/or treated with the odor control compositions in which the treated textile binds and/or neutralizes the organic malodor molecules for a prolonged period of time (e.g., up to twenty-five (25) wash cycles, for several months, for several years, or any combination thereof). In certain additional aspects, the odor control composition is uniformly and/or homogeneously applied on the textile.

In certain aspects, the plant derived non-volatile triglycerides applied on the textile ranges from 0.5% percent weight on fabric (owf) to 5% owf, more preferably 0.75% owf to 3.5% owf, and most preferably 1% owf to 3% owf. In certain aspects the plant derived non-volatile triglycerides applied on the textile ranges from 1.5% percent weight on fabric (owf) to 6.5% owf, more preferably 1.75% owf to 5% owf, and most preferably 2% owf to 3% owf. In certain aspects, the zeolite applied on the textile ranges from 0.25% percent weight on fabric (owf) to 3% owf, more preferably 0.5% owf to 1.5% owf, and most preferably 0.75% owf to 1.25% owf. In certain aspects, the zeolite applied on the textile ranges from 0.5% percent weight on fabric (owf) to 6% owf, more preferably 0.5% owf to 5% owf, and most preferably 1% owf to 3% owf.

Also disclosed herein are dry textile material(s) having one of the above-mentioned compositions applied thereon, wherein the dry textile material and/or the composition applied thereon binds and neutralizes organic malodor molecules on the dry textile material for a prolonged period of time. In this aspect, the plant derived non-volatile triglycerides applied on the dry textile ranges from 0.5% percent weight on fabric (owf) to 5% owf, more preferably 0.75% owf to 3.5% owf, and most preferably 1% owf to 3% owf. In certain aspects the plant derived non-volatile triglycerides applied on the dry textile ranges from 1.5% percent weight on fabric (owf) to 6.5% owf, more preferably 1.75% owf to 5% owf, and most preferably 2% owf to 3% owf.In this aspect, the zeolite applied on the dry textile ranges from 0.25% percent weight on fabric (owf) to 3% owf, more preferably 0.5% owf to 1.5% owf, and most preferably 0.75% owf to 1.25% owf. In certain aspects, the zeolite applied on the dry textile ranges from 0.5% percent weight on fabric (owf) to 6% owf, more preferably 0.5% owf to 5% owf, and most preferably 1% owf to 3% owf.

In this aspect, the plant derived non-volatile triglycerides and zeolite are present on the dry textile material at a ratio of 3:1 to 1:3, 2:1 to 1:2 more preferably 1.5:1 to 1:1.5, most preferably 1:1. In this aspect, the dry textile material and/or the composition applied thereon binds and neutralizes ammonia, acetic acid, and isovaleric acid on the textile material when compared to an untreated textile material. In this aspect, the dry textile material binds and neutralizes 75% to 100% and more preferably 80% to 100% of ammonia when compared to an untreated textile material, and/or the dry textile material binds and neutralizes 75% to 100% and more preferably 80% to 100% of acetic acid when compared to an untreated textile material, the dry textile material binds and neutralizes 75% to 100% and more preferably 80% to 100% of isovaleric acid when compared to an untreated textile material, and/or the dry textile material binds and neutralizes 75% to 100%, and more preferably 80% to 100%, of nonenal and/or odor associated with the presence of nonenal, when compared to an untreated textile material. In certain aspects, the dry textile material binds and neutralizes 90% to 100% and more preferably 95% to 100% of ammonia when compared to an untreated textile material, and/or the dry textile material binds and neutralizes 20% to 70% and more preferably 30% to 70% of acetic acid when compared to an untreated textile material, and/or the dry textile material binds and neutralizes 20% to 70% and more preferably 30% to 70% of isovaleric acid when compared to an untreated textile material.

Also disclosed herein are methods of applying an odor control composition to a textile material comprising: (a) mixing 2 wt % to 10 wt % of the odor control concentrate (as disclosed above) with 90 wt % to 98 wt % of water thereby forming the odor control composition; (b) after step (a), applying, by a padding or exhaustion method, the odor control composition to a textile material; and (c) after step (b), drying, heat setting, and/or curing the textile material thereby forming a treated textile material that reduces, binds, and/or neutralizes odor molecules and/or odors associated with the presence of odor molecules. In certain aspects, the odor control composition is applied to the textile material via exhausting/an exhaustion method and subsequently dried such that the treated textile binds and/or neutralizes the organic malodor molecules for a prolonged period of time (e.g., up to twenty-five (25) wash cycles, for several months, for several years, or any combination thereof). The exhaustion process consists of adding the plant derived non-volatile triglycerides and high surface area essential minerals/zeolite solution and fabric to an exhaustion machine and it will gradually increase the temperature and gradually decrease the temperature over a desired timeframe. In other aspects, the odor control composition is applied to the textile material via a padding method and subsequently dried such that the treated textile reduces, binds, and/or neutralizes the organic odor/malodor molecules and/or odors associated with the presence of organic odor/malodor molecules for a prolonged period of time (e.g., up to twenty-five (25) wash cycles, for several months, for several years, or any combination thereof). The padding process requires applying the plant derived non-volatile triglycerides and high surface area essential minerals solution to a fabric and moving it through rollers then drying the fabric in the oven to cure. When the textile is either padded or exhausted with high heat and pressure the plant derived non-volatile triglycerides and high surface area essential minerals combination will be incorporated into the fabric (e.g., permanently incorporated) and will remain there for a prolonged period of time (e.g., a predetermined number of wash cycles).

In certain aspects, the odor molecules comprise ammonia, nonenal, isovaleric acid, acetic acid, or any combination thereof. In certain aspects, the odor molecules comprise at least two of ammonia, nonenal, isovaleric acid, and acetic acid. In certain aspects, the odor molecules comprise at least three of ammonia, nonenal, isovaleric acid, and acetic acid. In certain aspects, the odor molecules comprise each of ammonia, nonenal, isovaleric acid, and acetic acid. In certain aspects, at least an 80% reduction of ammonia, nonenal, isovaleric acid, and acetic acid is observed in the treated textile when compared with an untreated textile. In certain aspects, at least an 80% reduction of ammonia, at least an 83% reduction of nonenal, at least an 85% reduction of isovaleric acid, and at least a 95% reduction of acetic acid is observed in the treated textile when compared with an untreated textile.

In certain aspects, step (a) further comprises an alkali metal salt at a concentration ranging from 0.1 wt % to 0.8 wt % the odor control composition. In certain aspects, the alkali metal salt is sodium lactate or sodium bicarbonate. In certain aspects, the alkali metal salt is sodium lactate.

In certain aspects, the pH of the odor control composition of step (a) ranges from 5.0 to 7.5, more preferably 5.5 to 6.2. In certain aspects, pH of the odor control composition of step (a) does not exceed pH 7.0.

Also disclosed herein is a textile odor control composition comprising: (a) the odor control concentrate as disclosed above at a concentration of 2 wt % to 10 wt % of the textile odor control composition, (b) water at a concentration of 90 wt % to 98 wt % % of the textile odor control composition; and (c) an alkali metal salt, wherein: pH of the odor control composition of ranges from 5 to 7.5, more preferably 5.5 to 6.2. In certain aspects, wherein the plant derived non-volatile triglycerides and zeolite are present in at a ratio of 2:1 to 1:2, more preferably 1.5:1 to 1:1.5, most preferably 1:1. In certain aspects, the plant derived non-volatile triglycerides comprises castor oil. In certain aspects, the plant derived non-volatile triglycerides comprises at least two of aloe oil, castor oil, hemp seed oil, and flax seed oil. In certain aspects, the plant derived non-volatile triglycerides comprises aloe oil and castor oil. In certain aspects, the plant derived non-volatile triglycerides comprises aloe oil, castor oil, hemp seed oil, and flax seed oil. In certain aspects, the zeolite is chabazite, pentasil, or any combination thereof. In certain aspects, the alkali metal salt is present at a concentration ranging from 0.1 wt % to 0.8 wt % the odor control composition. In certain aspects, zeolite is always present at higher concentrations that the alkali metal salt. In certain aspects, the ratio of zeolite to alkali metal salt 2:1 to 20:1, more preferably 10:3 to 10:1. In certain aspects, the alkali metal salt is sodium lactate or sodium bicarbonate. In certain aspects, the alkali metal salt is sodium lactate. In further aspects, one or more surfactants, binder(s), thixotropic agent(s), dispersant(s), or any combination thereof may be further included to aid in dispersion of the components within the composition (e.g., concentrated and/or diluted compositions disclosed herein) and/or application and/or binding of the composition to the textile (e.g., homogeneous application onto the surface of the textile material and/or into the fibers of the textile material). In certain aspects, the textile odor control composition disclosed immediately above excludes dextrins, cyclodextrins, and/or highly branched cyclodextrins, as well as effervescent systems (e.g., systems that form/generate gas from, for example, an acid source and a carbon dioxide source). Furthermore, the disclose compositions are not laundry additives/laundry detergent additives intended for consumer use Embodiments of the invention can include one or more or any combination of the above features and configurations.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed.

DETAILED DESCRIPTION

The present invention will now be described more fully hereinafter with reference to the working examples in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

Further, the term "or" as used in this disclosure and the appended claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Throughout the specification and claims, the following terms take at least the meanings explicitly associated herein, unless the context dictates otherwise. The meanings identified below do not necessarily limit the terms, but merely provide illustrative examples for the terms. The meaning of "a," "an," and "the" may include plural references, and the meaning of "in" may include "in," "at," and/or "on," unless the context clearly indicates otherwise. The phrase "in one embodiment," as used herein does not necessarily refer to the same embodiment, although it may.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

"High surface area essential mineral (HSAEM)" includes a mineral having a specific surface area (SSA) of greater than 250 $m^2/g$ (ranges from 250 $m^2/g$ to 500 $m^2/g$ and more preferably 300 $m^2/g$ to 500 $m^2/g$). Examples of HSAEM(s) include clay and clay materials, and more particularly include zeolites and/or aluminosilicates, and most particularly chabazite and/or pentasil.

"Plant derived non-volatile triglycerides" disclosed herein are a mixture of saturated and polyunsaturated, 12 to 20-carbon fatty acids (C12-C20 fatty acids). "Plant derived" refers to the original of the triglycerides or oil; they are from vegetable origin in contrast to animal or synthetic origin. "Non-volatile" refers to triglycerides that do not evaporate at room temperature (25° C.), for example that have a boiling point above 100° C., preferably above 150° C., and more preferably above 200° C. The plant derived non-volatile triglycerides (which may also be referred to in this specification as essential oils or as oils) include castor oil, aloe oil, hemp seed oil, and flax seed oil, and more preferably included castor oil as a primary plant derived non-volatile triglyceride in the disclosed compositions, and if present, aloe oil as a secondary plant derived non-volatile triglyceride. In certain aspects, castor oil is the primary plant derived non-volatile triglyceride, which is a non-aromatic oil. The fatty acid profile of castor oil includes at least 85 wt % to 95 wt % ricinoleic acid as well as other fatty acids therein. For example, other fatty acids included in castor oil in addition to ricinoleic acid include linoleic acid, oleic acid, stearic acid, palmitic acid, linolenic acid, and dihydroxystearic acid, which comprise the remaining 5 wt % to 15 wt % (Safety Data Sheet, Alnor, August 2023) of castor oil. Castor oil has a boiling point above 300 degrees Celsius and a flash point above 230 degrees Celsius. In addition, castor oil has a hydroxyl content of 160-168 (Technical Data Sheet, Alnor, April 2012). In certain aspects, aloe oil is the secondary plant derived non-volatile triglyceride within the disclosed composition. Aloe oil includes an aromatic fatty acid profile. The aloe oil used herein is comprised of 0.1-10% Aloe Barbadensis Leaf Extract, and 90-99.9% canola oil (Cosmetic Ingredient Information Sheet, HALLSTAR, February 2020) and may further include an antioxidant (i.e., 0.1-0.4% tocopherol). Aloe Barbadensis Leaf Extract contains various compounds, including phenolic compounds and dicarboxylic acids. The fatty acid profile of canola oil contains, on average, 60 wt % oleic acid, 20 wt % linoleic acid, and 10 wt % linolenic acid (Reference Module in Food Science, V. J. Barthet, 2016) with the remaining 10 wt % being additional fatty acids. Canola oil has a boiling point above 300 degrees Celsius and a flash point above 220 degrees Celsius (Safety Data Sheet, HALLSTAR, May 2015). In certain aspects, hemp seed oil and flax seed oil are other plant derived non-volatile triglycerides that may be included within the disclosed compositions. Hemp seed oil and flax seed oil are both non-aromatic oils. Hemp seed oil has a boiling point above 230 degrees Celsius and a flash point above 130 degrees Celsius (Safety Data Sheet, NHR Organic Oils, June 2017). Flax seed oil has a boiling point above 100 degrees Celsius and a flash point above 280 degrees Celsius (Safety Data Sheet, NHR Organic Oils, November 2020). The common fatty acids present in each of these plant derived non-volatile triglycerides are linoleic acid and linolenic acid.

"Owf" or percent on weight of fabric is generally used in the field and batch processes, the amount of chemical finish to be applied is usually expressed as a weight percentage based on the original fabric weight. This relationship is abbreviated as % owf (percent on weight of fabric), which is % OW=[(Weight of Chemical/Weight of Fabric)*100]/Wet pickup rate %. For example, if a chemical is to be applied at 3% owf to 400 kg of fabric, having a wet pickup rate=80%, then 15 kg of the chemical will be used (3% of 400 kg at 80% pickup).

"Permanently adhered" or "adhere for a prolong period of time" is used here to indicate that the composition remains in the textile for at least 25 wash cycles, which may be a period of months or even years, depending on the number of times it is washed.

Odor Control Concentrate Compositions

Disclosed herein are odor control concentrate compositions (pre-application to the textile material) that are applied (e.g., subsequently diluted and permanently applied via padding or exhaustion techniques) to and/or used to treat textile materials to reduce, bind and/or neutralize odor and/or organic malodor molecules (secreted and/or excreted from humans) on the textile material for a prolonged period of time (e.g., 25 wash cycles, several months, or up to a year). The disclosed concentrate compositions are environmentally friendly and are just as effective, if not more effective, for odor control and reduction, than the currently known heavy metal and nanomaterial formulations used in the textile field to form treated textile materials/treated textiles.

In particular, the odor control concentrate compositions include a combination of plant derived non-volatile triglycerides and zeolite(s). The odor control concentrate compositions disclosed herein further includes water and may further include alkali metal salt(s). The odor control concentrate compositions are liquids at ambient conditions, and are more preferably an emulsion (e.g., water in oil emulsion or oil in water emulsion depending on water and oil content of the particular concentrate composition).

The plant derived non-volatile triglycerides within the odor control concentrate compositions are included at a concentration ranging from 18 wt % of the composition to 40 wt % of the composition in which any endpoint falling therein may serve as an endpoint for additional ranges, additional ranges may include, for example, from 20 wt % to 35 wt %, from 25 wt % to 40 wt %, from 25 wt % to 30 wt %, from 18 wt % to 30 wt %. In certain aspects, the plant derived non-volatile triglycerides include aloe oil, castor oil, hemp seed oil, flax seed oil, canola oil, or any combination thereof. In certain aspects, the plant derived non-volatile triglycerides comprises at least two of aloe oil, castor oil, hemp seed oil, canola oil, and flax seed oil. In certain aspects, plant derived non-volatile triglycerides comprises at least three of aloe oil, castor oil, hemp seed oil, canola oil, and flax seed oil. When there are two plant derived non-volatile triglycerides present in the compositions, the oils may be present in a 5:1 to 1:5 ratio, a 3:1 to 1:3 ratio, or a 1:1 ratio. In certain aspects, the plant derived non-volatile triglycerides comprises aloe oil, castor oil, hemp seed oil, and flax seed oil. As discussed further below, when diluted and applied to a textile material, each of the above-mentioned plant derived non-volatile triglycerides function to control odor by binding, reducing, and/or neutralizing odor molecules (e.g., isovaleric acid, ammonia, nonenal, and/or acetic acid) and/or odor associated with the presence of these odor molecules while concurrently functioning to adhere the zeolite(s) to the textile material. Moreover, the zeolite(s) included within the odor control concentrate compositions are included at a concentration ranging from 10 wt % of the composition to 50 wt % of the composition in which any endpoint falling therein may serve as an endpoint for additional ranges, additional ranges may include, for example, from 15 wt % to 50 wt %, from 20 wt % to 45 wt %, from 25 wt % to 40 wt %, from 30 wt % to 40 wt %. Zeolites are preferred due to their high surface area and capabilities to bind, neutralize, and/or reduce odor molecules (e.g., ammonia, nonenal, acetic acid, and/or isovaleric acid) and/or odors associated with the presence of odor molecules. In certain preferred aspects, the zeolite is chabazite and/or pentasil. Moreover, the zeolite(s) disclosed herein are provided in the disclosed compositions as polydisperse particles ranging from 0.1 µm to 10 µm, more preferably from 0.5 µm to 5 µm, which advantageously allows the disclosed plant derived non-volatile triglycerides to permanently fix and/or cure the zeolites on and/or within the textile material. Zeolite particles exceeding the above-mentioned highest endpoint should be avoided as they are coarse and will be easily worn off of the textile material post-application thereto (as well as negatively impact the haptic/tactile feel), which will disadvantageously result in reduced odor control; and zeolite(s) particles falling below the above-mentioned lowest endpoint should be avoided due to regulatory restriction prohibiting the use of nanoparticles on textile materials (due to potential skin absorption and toxicological effects).

In certain aspects, the odor control concentrate composition comprises aloe oil, castor oil, hemp seed oil, flax seed oil, or any combination thereof present at a concentration ranging from 25 wt % to 40 wt %. of the overall weight of the composition; and a zeolite present at a concentration ranging from 10 wt % to 50 wt % of the overall weight of the composition.

In certain aspects, the plant derived non-volatile triglycerides and zeolite(s) are present in at a ratio of 3:1 to 1:3, 2:1 to 1:2 more preferably 1.5:1 to 1:1.5, most preferably 1:1 relative to one another. The plant derived non-volatile triglycerides disclosed herein, when present in the above-mentioned concentrations and/or ratios, advantageously function to adhere (e.g., permanently adhere and/or adhere for a prolong period of time-25 wash cycles, months or years) the zeolite(s) to the textile material (during and post-application of the compositions to the textile material) thereby achieving the desired odor control and reduction by binding and/or neutralizing the organic molecules while concurrently functioning to adhere the zeolite(s) to the textile material.

In certain aspects, the odor control concentrate composition further includes an alkali metal salt in which the alkali metal salt is preferably sodium lactate, sodium bicarbonate, or a combination. When present in the concentrate composition, the alkali metal salt is included at a concentration ranging from 1.5 wt. % to 15 wt. % of the odor control concentrate compositions. The alkali metal salt aids in maintaining a pH of the odor control concentrate between pH 4.0 to 7.5. The alkali metal salt aids in the capture of IVA, nonenal, and acetic acid odorants in the treated textile/textile material. In certain aspects, zeolite is always present at higher concentrations that the alkali metal salt, and the ratio of zeolite to alkali metal salt 2:1 to 20:1, more preferably 10:3 to 10:1. If the concentration of the alkali metal salt exceeds the disclosed amounts in the concentrate composition, and ultimately on the treated textile material, the zeolites ability to capture odors, particularly ammonia, is significantly reduced and the pH of the treatment may become to alkaline which will interfere with the integrity and visual properties of the textile material.

The odor control concentrate composition may further include one or more surfactants, binders, thixotropic agents, dispersants, defoamers or any combination thereof to aid in dispersion of the above mentioned chemical components within the odor control concentrate compositions. The one or more surfactants may include, but are not limited to, ethoxylated alcohols, polyethylene glycol dilaurates or dioleates, sorbitan laurates, oleates, or stearates, alkyl or aryl ethoxy sulfates, sulfonates and alkyl sulfates, alcohol ethoxylate/propoxylate copolymers, at a concentration ranging from 0.5 wt % to 8 wt % within the odor control concentrate compositions. Likewise, the dispersants within the odor control concentrate composition may include, but are not limited to, acrylic resins, maleated soybean oils, capric triglyceride, polylactate/ricinoleate copolymers, polyethylene glycols, stearth 20, polyhydroxysteric acid ceteary glucoside, polyglycerol stearate, polyglycinyl distearate, sodium stearoyl lactylate, distearyldimethyl ammonium chloride, and othersat a concentration ranging from 1 wt % to 8 wt % within the odor control concentrate compositions. Likewise, the binders within the odor control concentrate composition may include, but are not limited to, acrylic binders, polyester binders, polyurethane binders, polyolefin binders, styrene acrylic binders, at a concentration ranging from 10 wt % to 30 wt % within the odor control concentrate compositions. Likewise, the thixotropic agents within the odor control concentrate composition may include, but are not limited to, a synthetic or naturalphyllosilicate, clay, cellulose, acrylates, carbomers, xanthan gum, pyrogenic silica, polyquaternium, polysorbate; at a concentration ranging from 0.01 wt % to 1 wt % within the odor control concentrate compositions. Likewise, the defoamers within the odor control concentrate may include, but are not limited to, polysiloxanes, silicone emulsions or oils, alkyl polyacrylates, and alkylaryl polyethers, While the odor control concentrate may be an oil in water emulsion or a water in oil emulsion, in certain embodiments an oil in water emulsion is preferred. When preparing either type of emulsion, two separate phases are initially prepared, which are the oil phase and the aqueous phase. Within the oil phase, zeolites are mixed with the plant derived non-volatile triglycerides along with dispersants, surfactants, and defoamers. While mixing, these components are concurrently milled or homogenized to reduce zeolite size. In particular, high shear mixing/milling continues until the zeolites are polydisperse particles ranging from 0.1 µm to 10 µm, more preferably from 0.5 µm to 5 µm. Moreover, high shear mixing of the zeolites with the plant derived non-volatile triglycerides along with dispersants and surfactants occurs for a predetermined time period such that the zeolite particles are coated (e.g., partially or completely coated, with complete coating being preferred) with the plant derived non-volatile triglycerides so that the zeolite will remain in the internal phase when emulsified within the below mentioned aqueous phase. When further preparing the above mentioned emulsions, an aqueous phase is prepared separately from the oil phase. The aqueous phase includes water with surfactants (preferably non-ionic surfactants) and thixotropes mixed therein. Non-ionic surfactant(s) are included in the aqueous phase to make an oil in water emulsion. Non-ionic surfactants preferably have an HLB value of 8-13. Examples of non-ioninc surfactants include but are not limited to ethoxylated alcohols, polyoxyethylene castor oils, polyoxyethylene hydronated castor oils, polyethylene glycol dilaurates or dioleates, sorbitan laurates, oleates, or stearates, Thixotropes are useful to prevent syneresis of the emulsion-They provide a physical barrier to prevent the emulsion droplets from colliding in to one another, increasing the stability of the emulsion.

After preparing the above mentioned oil and aqueous phases, the two phases are mixed together using a homogenizer (Silverson L5M-A), between 2500-5000 rpm, for 15-45 minutes to form either the oil in water emulsion or the water in oil emulsion, which depends on and is determined by the overall oil content and water content in the emulsion. During this mixing/homogenizing step, the alkali metal salt(s) as disclosed above can be added at the concentrations disclosed above. The two phases are mixed for the predetermined time period until, for the oil in water emulsion, the oil phase is homogeneously mixed within the aqueous phase thereby forming the odor control concentrate compositions disclosed above having the concentrations and components disclosed above, or for the water in oil emulsion, the aqueous phase is homogeneously mixed with the oil phase forming the odor control concentrate compositions disclosed above having the concentrations and components disclosed above.

As shown within the Working Examples, certain odor control concentrate compositions disclosed herein are oil in water emulsions including at least 36% water as a diluent, the plant derived non-volatile triglycerides at a concentration ranging from 18 wt % to 40 wt % of the composition, more preferably from 18 wt % to 30 wt %, the zeolite at a concentration ranging from 10 wt % to 50 wt % of the composition, more preferably from 10 wt % to 30 wt %, most preferably 12.5 wt % to 20 wt %, and in certain aspects, the alkali metal salt may be included within the concentrate composition at any of the above concentrations. Moreover, the zeolite coated with the plant-derived non-volatile triglyceride is preferably homogenously dispersed within the aqueous phase of oil in water emulsion such that the zeolite does not precipitate out of the odor control concentrate composition.

Method of Applying The Odor Control Compositions To A Textile Material

The odor control concentrate composition disclosed above may be diluted, with for example water, to form an odor control composition that is subsequently applied (permanently applied) to a desired textile material via a padding or exhausting method. When proceeding in this manner, approximately 0.2 wt % to 10 wt % of the above-mentioned odor control concentrate composition is diluted in water (e.g., 90 wt % to 99.8 wt %) and this dilution (odor control composition) is subsequently applied to the textile material via the padding method or the exhausting method. After application of the composition onto the textile material, the textile material is subjected to drying, heat setting, and/or curing thereby forming the dry textile material (also referred to as the "treated textile material") that reduces, binds, and/or neutralizes odor molecules and/or odors associated with the presence of odor molecules.

For example, when using the padding method, the pad bath is made by combining the concentrate of the odor control/textile coating composition and water, which is approximately 2-10% concentrate of the composition and 90-98% water. The pad bath should have a pH between 4.0 and 7.5. The pad bath is padded onto the desired textile material using a continuous roller wherein the textile is submerged in the padding path from one to fifteen seconds. The padded textile is subsequently cured/dried at a temperature ranging from 130° C. to 180° C. in an infrared (IR) drier for a time period from 30 seconds to 5 minutes to obtain a dry textile material that neutralizes odor and/or organic malodor molecules (secreted and/or excreted from humans) on the textile material for a prolonged period of time (e.g., 25 wash cycles, several months, or up to a year).

For example, in the exhausting method, the exhaustion bath is made by combining the concentrate of the odor control/textile composition and water, which is approximately 0.2-0.5% concentrate and 99.5-99.8% water. The exhaustion bath should have a pH between 4.0 and 6.5. The exhaustion may be performed in a beaker dyeing machine that includes the desired textile material, e.g., Lobomat BFA-24 Werner Mathis AG. The exhaustion conditions may include the following: liquor ratio of 10 to 1, exhaustion temperature at 65° C. to 135° C., dwell time at the exhaustion temperature was 40 minutes, and the heating and cooling rate was 2° C./minute. After the exhaustion, the treated textile materials were rinsed and then cured/dried in an IR drier at a temperature ranging from 130° C. to 180° C. for a time period from 30 seconds to 5 minutes to obtain a dry textile material having that neutralizes odor and/or organic malodor molecules (secreted and/or excreted from humans) on the textile material for a prolonged period of time (e.g., 25 wash cycles, several months, or up to a year).

In certain aspects, the plant derived non-volatile triglycerides and more particularly the castor oil and/or aloe vera oil provides multiple benefits during and post-application of the odor control composition (i.e., the diluted form of the odor control concentrate composition) to the textile material. In particular and in view of the ratios and/or concentrations disclosed herein, during application to the textile material, the plant derived non-volatile triglycerides and more particularly the castor oil and/or aloe vera oil acts as a co-dispersant for the zeolite. At the ratios and/or concentrations disclosed herein, the plant derived non-volatile triglycerides and more particularly the castor oil and/or aloe vera oil encapsulates the zeolite and stabilizes the zeolite during application of the composition to the textile material. The plant derived non-volatile triglycerides and more particularly the castor oil and/or aloe vera oil further acts as a carrier for the zeolite, allowing the zeolite to penetrate within and/or adhere to the textile material during and/or post-application of the odor control composition to the textile material. Moreover, the plant derived non-volatile triglycerides and more particularly the castor oil and/or aloe vera oil advantageously acts as a plasticizer softening the textile material during application of the composition thereby facilitating deeper penetration of, for example, the zeolite, alkali metal salt(s), and non-volatile triglycerides into the textile material, which in turn provides for greater prolonged odor control (e.g., binding, neutralizing, and reducing ammonia, nonenal, isovaleric acid, and/or acetic acid and/or odors associated with the presence of ammonia, nonenal, isovaleric acid, and/or acetic acid) within the textile material. In certain aspects, zeolite is large enough that it only partially penetrates the textile fiber, allowing for a portion of the zeolite to be exposed on the textile/fabric surface and available to capture odorants. The plant derived non-volatile triglycerides and more particularly castor oil and/or aloe vera oil further improves the lubricity of the textile material (e.g., fabric(s)) both during and post-application of the composition to the textile material by reducing and/or minimizing tactile imperfections (e.g., surface roughness and/or abrasiveness) associated with the presence of zeolite on the textile material's outer surface (e.g., textile fabric's outer surface). This further improves dry crocking and minimizes friction of the textile material's outer surface thereby preventing and/or reducing premature wear of the textile material post-application of the odor control composition.

Moreover, the alkali metal salts included within the composition aid in the capture of isovaleric acid, acetic acid, and nonenal ororants during and post-application of the composition to the textile. As alluded to above, sodium lactate and/or sodium bicarbonate may be used as the alkali metal salt. However, sodium lactate is the most preferred alkali metal salt, considering that a treated fabric/treated textile must have a pH of 4.0-7.5. Fabric pH should be between 4-7.5 so that fabric will not irritate the skin. Moreover, when fabric pH exceeds 7.5, phenolic yellowing is likely to occur, which is aesthetically displeasing. Conversely, when fabric pH drops below 4, dye(s) within the textile material, for example fabric, becomes soluble and leaches out of the fabric. In particular, sodium bicarbonate has a pKa~6.4, which is much higher than the sodium lactate's pKa. During padding or exhaustion and due to its relatively high pKa, sodium bicarbonate's conjugate acid (carbonic acid) will quickly react with water to form carbon dioxide as pH approaches 6.4 or lower. Pad baths formulated with sodium bicarbonate tend to have a pH range of 6.75-7.25, and result in textiles (e.g., treated textiles and/or treated fabrics) having a pH range of 7.0-7.75. Thus, the upper pH end (e.g., pH 7.51-7.75 of textile materials treated with compositions having sodium bicarbonate fall outside of the preferred treated fabric pH range of pH 4.0-7.5. In contrast, Sodium lactate has a pKa~3.8, which is much lower than sodium bicarbonate's pKa, and sodium lactate converts to its conjugate acid (lactic acid) at a much lower pH (e.g., as pH approaches 3.8 or lower). Pad baths formulated with sodium lactate tend to have a pH range of 5.0-6.0, and result in textiles (treated textiles and/or treated fabrics) having a pH range of 6.0-6.75, which falls squarely within the treated fabric pH range of 4.0-7.5. Furthermore, when the pH of a textile material (e.g., garments) exceeds 7.5, human skin irritation often occurs if in contact with the textile material for prolonged periods of time due to its basicity.

Use Of The Compositions

Further disclosed herein are uses of the compositions for permanent application on a textile material for odor control. The aspects disclosed above for the composition and method are also applicable to the uses.

Textile Materials Having The Odor Control Compositions Thereon

Further disclosed herein are the dry textile material(s) (also referred to as the "treated textile" or "treated textile material") having one of the above-mentioned compositions applied thereon via, for example, the above-mentioned padding or exhausting methods. The dry textile material having the odor control/textile coating composition applied thereon binds, neutralizes, and/or reduces odors associated with organic odor/malodor molecules on the dry textile material for a prolonged period of time especially when compared with the same dry textile materials not treated with the compositions disclosed herein (and/or having the compositions disclosed herein applied thereon).

In this aspect, the dry textile material includes the plant derived non-volatile triglycerides applied thereon at a concentration ranging from 0.5% percent weight on fabric owf) to 5.0% owf, more preferably 0.75% owf to 3.5% owf, and most preferably 1% owf to 3% owf, or 1.5% or 1.75% to 2% owf, hand the zeolite applied on the textile ranges from 0.25% percent weight on fabric (owf) to 3% owf, or from 0.25% owf to 2% owf or 0.25% owf to 1.75 owf, more preferably 0.5% owf to 1.5% owf, and most preferably 0.75% owf to 1.25% owf, In this aspect, the alkali metal salt ((e.g., sodium bicarbonate and sodium lactate) applied on the textile ranges from 0.08% owf to 0.6% owf, from 0.09% owf to 0.5% owf, from 0.1% owf to 0.5% owf, from 0.1% owf to 0.4% owf, from 0.1% owf to 0.3% owf, from 0.1% owf to 0.2% owf, and 0.1% owf to 0.15% owf. In this aspect, the plant derived non-volatile triglycerides and zeolite are present on and/or within the dry textile material at a ratio of 3:1 to 1:3, 2:1 to 1:2 more preferably 1.5:1 to 1:1.5, most preferably 1:1.

In view of the above mentioned concentrations and ratios, the dry textile material and/or the composition applied thereon controls odors for prolonged periods of time by binding neutralizing, and/or reducing odor associate with ammonia, acetic acid, isovaleric acid, and/or nonenal on the textile material especially when compared to an untreated textile material. In particular, the dry textile material binds and neutralizes 75% to 100% and more preferably 80% to 100% of ammonia when compared to an untreated textile material, and/or the dry textile material binds and neutralizes 75% to 100% and more preferably 80% to 100% of acetic acid when compared to an untreated textile material, the dry textile material binds and neutralizes 75% to 100% and more preferably 80% to 100% of isovaleric acid when compared to an untreated textile material, and/or the dry textile material binds and neutralizes 75% to 100% and more preferably 80% to 100% of nonenal when compared to an untreated textile material. In certain aspects, the plant derived non-volatile triglycerides and more particularly the castor oil and/or aloe oil binds, neutralizes, and/or reduces odors associated with the presence of isovaleric acid and/or nonenal.

In certain preferred aspects, the textile materials disclosed herein, including the dry textile materials, are either woven or non-woven textile materials. In certain preferred embodiments, the textile materials and/or dry textile materials are knitted/woven fabrics, including, polyester, nylon, rayon, cotton, or any combination thereof. In certain aspects, the textile material/dry textile material includes a fabric weight ranging from 20-400 gsm (grams per square meter). It should be further appreciated that heavier weighted fabrics will absorb more of the above disclosed compositions (e.g., during and post-padding and/or during and post-exhaustion) resulting in a dry textile material having better odor control/capture for prolonged periods of time.

WORKING EXAMPLES

Table 1 provides Exemplary Compositions (i.e., Compositions 3-6 abbreviated "Comp #3", "Comp #4", "Comp #5", and "Comp #6" in Tables 1-3) of those disclosed herein as well as Comparative Formulations (i.e., Comparative Formulations 1-2 abbreviated "Comp #1", and "Comp #2" in Tables 1-3). Each composition disclosed within Table 1 (Comparative Compositions 1-2 and Exemplary Compositions 3-6) were applied to textured polyester interlock knit fabric, produced from filament yarn, at 5% owf via padding methods at 150° C. for 120 seconds. Fabric weight is 106 g/m$^2$. Fabric wet pick-up rate was 100 wt. %. Polyester fabric is #703, Item #1405003, via Test Fabrics. Individual samples were A4 size (210 mm×297 mm). As shown in Table 1, Comparative Compositions 1 and 2 (abbreviated "Comp #1", and "Comp #2" in Tables 1-3) lack alkali salts (e.g., sodium bicarbonate and sodium lactate) when compared to the Exemplary Compositions 3-6 (abbreviated "Comp #3", "Comp #4", "Comp #5", and "Comp #6" in Tables 1-3). The textiles treated with each composition have owf values as shown in Table 2.

Biovera® Aloe Vera Oil was used in Composition #1. Biovera® Aloe Vera Oil (Safety Data Sheet Issue date Dec. 11, 2015, pages 1-8, including canola oil (CAS No. 120962-03-0) and aloe barbadensis leaf extract (CAS No. 85507-69-3)). Castor oil was used in each composition, and was sourced from Alnor (Safety Data Sheet Issue date Aug. 2, 2023). Laponite® RD was sourced from BYK (Safety Data Sheet, print date: May 10, 2022). E-Sperse® 325 sourced from Ethox Chemicals, LLC (Technical Bulletin). Sodium lactate (60%) sourced as Galaflow SL from Galactic (Material Safety Data Sheet, revised Dec. 16, 2008; Technical Data Sheet, March 2024 Edition). Printol HPB was sourced from DyStar® (Product Data Sheet, issue date 05/2008).

TABLE 1

| | | Comp#1 (Water-in-oil) | Comp#2 (Water-in-oil) | Comp#3 (Water-in-oil) | Comp#4 (Water-in-oil) | Comp#5 (Oil-in-water) | Comp#6(Oil-in-water) |
|---|---|---|---|---|---|---|---|
| Castor Oil (Cold-pressed) | Active | 20.00% | 33.33% | 20.00% | 20.00% | 20.00% | 20.00% |
| Biovera Aloe Oil | Active | 13.33% | | | | | |

TABLE 1-continued

|  |  | Comp#1 (Water-in-oil) | Comp#2 (Water-in-oil) | Comp#3 (Water-in-oil) | Comp#4 (Water-in-oil) | Comp#5 (Oil-in-water) | Comp#6 (Oil-in-water) |
| --- | --- | --- | --- | --- | --- | --- | --- |
| HCZC Zeolite | Active | 13.00% | 13.00% | 15.00% | 16.00% | 16.00% | 16.00% |
| $NH_4$CHZP800 Zeolite | Active | 7.00% | 7.00% |  |  |  |  |
| Hydropalat ® WE 3136 (PEG and PPG block copolymer) | Surfactant | 4.00% | 4.00% | 4.00% | 4.00% | 1.06% | 1.06% |
| Ethal ® LA-4 (Linear alcohol ethoxylated) | Surfactant | 1.30% | 1.33% | 1.50% | 1.50% | 1.04% | 1.04% |
| E-Sperse ® 325 (a non-ionic, non-polar emulsifier and pigment dispersion) | Dispersant |  |  |  |  | 4.00% | 4.00% |
| Deionized $H_2O$ | Diluant | 20.97% | 20.94% | 39.50% | 38.50% | 37.50% | 37.50% |
| Laponite ® RD (synthetic phyllosilicate) | Thixotrope | 0.10% | 0.10% |  |  | 0.40% | 0.40% |
| Printol HFB Mod (acrylic emulsion) | Binder | 20.00% | 20.00% | 20.00% | 20.00% | 20.00% | 20.00% |
| Texipol ® 63-510 (acrylic copolymer) | Thixotrope | 0.30% | 0.30% |  |  |  |  |
| $NaHCO_3$ | Active |  |  | 0.1% owf | 0.15% owf | 0.1% owf |  |
| Sodium Lactate (60%) | Active |  |  |  |  |  | 0.5% owf |

TABLE 2

|  | Comp#1 | Comp#2 | Comp#3 | Comp#4 | Comp#5 | Comp#6 |
| --- | --- | --- | --- | --- | --- | --- |
| Castor Oil (Cold-pressed) | 1.00% | 1.67% | 1.00% | 1.00% | 1.00% | 1.00% |
| Biovera Aloe Oil | 0.67% |  |  |  |  |  |
| HCZC Zeolite | 0.65% | 0.65% | 0.75% | 0.80% | 0.80% | 0.80% |
| $NH_4$CHZP800 Zeolite | 0.35% | 0.35% |  |  |  |  |
| Printol HFB Mod | 1.00% | 1.00% | 1.00% | 1.00% | 1.00% | 1.00% |
| $NaHCO_3$ |  |  | 0.1% | 0.15% | 0.1% |  |
| Sodium Lactate |  |  |  |  |  | 0.5% |

After application to polyester substrates, the reduction in four major types of odorous compounds were measured for each of the compositions. Isovaleric acid reduction was measured by ISO 17299-3. Ammonia reduction was measured by ISO 17299-2. Acetic acid reduction was measured by ISO 17299-2, and nonenal reduction was measured by ISO 17299-3. As shown in Table 3, compositions 1 and 2, which lack sodium bicarbonate and sodium lactate, the reduction in acetic acid odor was low compared to compositions 3-6. Compositions having both castor oil and a zeolite, in combination with either sodium bicarbonate or sodium lactate showed significant reduction in each of ammonia, nonenal, isovaleric acid, and acetic acid odor reduction.

TABLE 3

|  | Ammonia Reduction | Nonenal Reduction | Isovaleric Acid Reduction | Acetic Acid Reduction |
| --- | --- | --- | --- | --- |
| Comp#1 | 90.3% | 91.3% | 82.3% | 53.3% |
| Comp#2 | 92.7% | 91.3% | 81.7% | 53.3% |
| Comp#3 | 88.3% | 90.5% | 85.4% | 77.0% |
| Comp#4 | 80.0% | 82.9% | 86.7% | 95.0% |
| Comp#5 | 78.3% | 82.0% | 79.7% | ND* |
| Comp#6 | 80.0% | 84.3% | 83.5% | ND* |
| Untreated PET | 7.0% | 51.0% | 26% | 1.0% |

*ND: Not Determined

The treated textile material was evaluated for wash durability using laundering conditions as specified in PHX AP0701. The treated textile was washed in ten cycles (HL). Each cycle was a 2 kg total load at least 40° C. using 20 g ECE-Reference Detergent 98 with Optical Brightener, followed by low tumble dry. Two textile materials, each treated with Comp #5 as described above, were evaluated both before and after the 10 wash cycles. The odor reduction retention results are shown in Table 4. As shown, the treated textile material maintains from 27.4% to 93.9% of its odor retention activity after 10 home launderings, which exhibits a significant improvement over the untreated PET even after 10 home launderings.

TABLE 4

| % Retention of Odor Reduction after 10 HL | Ammonia Reduction | Nonenal Reduction | Isovaleric Acid Reduction | Acetic Acid Reduction |
| --- | --- | --- | --- | --- |
| Upper range | 50.5% | 77.2% | 79.0% | 93.9% |
| Lower range | 27.4% | 65.7% | 88.3% | 83.1% |

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. A dry textile material having an odor control composition permanently applied thereon, the odor control composition comprising:
   (a) a plant derived non-volatile triglyceride present at a concentration ranging from 18 wt % to 40 wt % of the overall weight of the composition; and
   (b) a zeolite present at a concentration ranging from 10 wt % to 50 wt % of the overall weight of the composition;
   wherein the dry textile material and/or the composition applied thereon reduces, binds, and/or neutralizes odors from odor molecules on the dry textile material for a prolonged period of time;
   wherein the odor control concentrate composition further comprises an alkali metal salt in which the alkali metal salt is sodium lactate, sodium bicarbonate, or a combination thereof.

2. The dry textile material according to claim 1, wherein the plant derived non-volatile triglyceride applied on the dry textile material ranges from 0.5% owf to 5% owf, and the zeolite applied on the dry textile material ranges from 0.25% owf to 3% owf.

3. The dry textile material according to claim 1, wherein the plant derived non-volatile triglyceride and zeolite are present in at a weight ratio of 2:1 to 1:2.

4. The dry textile material according to claim 1, wherein the dry textile material reduces, binds, and/or neutralizes ammonia, acetic acid, isovaleric acid, and nonenal and/or odors associated with the presence of ammonia, acetic acid, isovaleric acid, and nonenal on the textile material when compared to an untreated textile material.

5. The dry textile material according to claim 4, wherein the dry textile material reduces, binds, and/or neutralizes 75% to 100% of ammonia and/or odor associated with the presence of ammonia when compared to an untreated textile material, and/or the dry textile material binds and neutralizes 75% to 100% of acetic acid and/or odor associated with the presence of acetic acid when compared to an untreated textile material, and/or the dry textile material binds and neutralizes 75% to 100% of isovaleric acid and/or odor associated with the presence of isovaleric acid when compared to an untreated textile material, and/or the dry textile material binds and neutralizes 75% to 100% of nonenal and/or odor associated with the presence of nonenal when compared to an untreated textile material.

* * * * *